(12) United States Patent
Crouzen et al.

(10) Patent No.: US 6,538,435 B2
(45) Date of Patent: Mar. 25, 2003

(54) METHOD FOR DETECTING AN ANOMALY IN AN OBJECT OF ELECTRICALLY CONDUCTIVE MATERIAL ALONG FIRST AND SECOND DIRECTION AT INSPECTION POINTS

(75) Inventors: Paulus Carolus Nicolaas Crouzen, Amsterdam (NL); Mark Theodoor Looijer, Amsterdam (NL); Johan van der Steen, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 09/931,979

(22) Filed: Aug. 17, 2001

(65) Prior Publication Data

US 2002/0097045 A1 Jul. 25, 2002

(30) Foreign Application Priority Data

Aug. 24, 2000 (EP) .............................................. 00307299

(51) Int. Cl.⁷ ........................ G01R 33/12; G01N 27/82; G01N 27/90
(52) U.S. Cl. ........................ 324/232; 324/240; 324/242
(58) Field of Search ................................. 324/240, 239, 324/238, 242, 220, 227, 229, 230, 262, 232

(56) References Cited

U.S. PATENT DOCUMENTS 5,485,084 A * 1/1996 Duncan et al. ............. 324/225
6,291,992 B1 * 9/2001 Van Andel et al. ......... 324/240

FOREIGN PATENT DOCUMENTS

| EP | 0860698 | 8/1998 |
| JP | 59225348 | 12/1984 |
| JP | 08334498 | 12/1996 |
| WO | 95/00840 | 1/1995 |

OTHER PUBLICATIONS

European Search Report with Annex, examined by G. Kempf, dated Feb. 1, 2001.

* cited by examiner

Primary Examiner—Edward Lefkowitz
Assistant Examiner—Reena Aurora

(57) ABSTRACT

Detecting the presence of an anomaly in or near an object using a probe comprises:
  a) selecting a set of points on the near surface which are to be inspected, and selecting a first direction and a second direction;
  b) selecting a first inspection point from the set;
  c) positioning the probe at the selected inspection point in the first direction, inducing eddy currents in the object and determining a characteristic value of the electromagnetic field;
  d) positioning the probe in the second direction at the selected inspection point, inducing eddy currents in the object and determining a characteristic value of the electromagnetic field;
  e) selecting a next inspection point from the set and repeating steps c) and d) until all inspection points have had their turn; and
  f) inferring that an anomaly is present at an inspection point if a combination of the characteristic values in the first and second direction deviates significantly from a norm.

20 Claims, 2 Drawing Sheets

METHOD FOR DETECTING AN ANOMALY IN AN OBJECT OF ELECTRICALLY CONDUCTIVE MATERIAL ALONG FIRST AND SECOND DIRECTION AT INSPECTION POINTS

BACKGROUND OF THE INVENTION

1. Field of the Invention

The present invention relates to detecting the presence of an anomaly in or near an object of electrically conducting material by means of eddy currents induced in the object.

The object can be a plate, such as a support plate or a shell, such as a wall. The electrically conducting material can be carbon steel or stainless steel. Suitably, the anomaly is a longitudinal anomaly, for example a crack or a frame element for supporting the plates that form the hull of a ship. In case of a crack, the crack can be in a vessel wall, a wall of a pipeline or a support plate of a bridge.

2. Description of Related Art

International patent application publication No. 95/00 840 discloses a method of detecting cracks in an object of electrically conducting material. The known method comprises inducing an eddy current into a portion of the object with an abruptly changing magnetic field; while the induced eddy current decays in the object portion, detecting the decay of the induced eddy current; determining with respect to time the derivative of the decay of the induced eddy current; determining a value from the derivative which is representative of the thickness of the portion; determining, by use of a magnetic flux leakage technique, the wall thickness of the object portion; and inferring that a plurality of cracks is present where a reduction in wall thickness is indicated by the derivative of the decay and no reduction in wall thickness is indicated with the magnetic flux technique.

Thus, in the known method, two different techniques are required to determine the presence of a crack.

SUMMARY OF THE INVENTION

It is an object of the present invention to provide a method of detecting cracks in an object of electrically conducting material wherein only one inspection technique is used.

To this end the present invention provides a method of detecting the presence of an anomaly in or near an object of electrically conducting material using a probe, which probe comprises a transmitter for inducing eddy currents in the object in a footprint area that is not rotational symmetric, and a receiver system for providing a signal indicative of the strength of an electromagnetic field or of changes of the strength of an electromagnetic field, which method comprises the steps of:

a) selecting a set of points on the near surface of the object which are to be inspected;

b) selecting a first inspection point from the set, and selecting a first direction and a second direction that differs from the first direction;

c) positioning the probe at the selected inspection point, activating the transmitter to induce eddy currents in the object such that the footprint is directed in the first direction by activating the transmitter, and determining a characteristic value $\Phi_1$ of the electromagnetic field generated by the eddy currents;

d) activating the transmitter to induce eddy currents in the object such that the footprint is directed in the second direction by activating the transmitter, and determining a characteristic value $\Phi_2$ of the electromagnetic field generated by the eddy currents;

e) selecting a next inspection point from the set and repeating steps c) and d) until all inspection points have had their turn; and f) inferring that an anomaly is present at an inspection point if a combination of the characteristic values $\Phi_1$ and $\Phi_2$ pertaining to the first and second direction deviates significantly from a norm.

BRIEF DESCRIPTION OF THE DRAWINGS

The invention will now be described in more detail by way of example with reference to the accompanying drawings, wherein.

DESCRIPTION OF THE PREFERRED EMBODIMENTS

Figure 1:
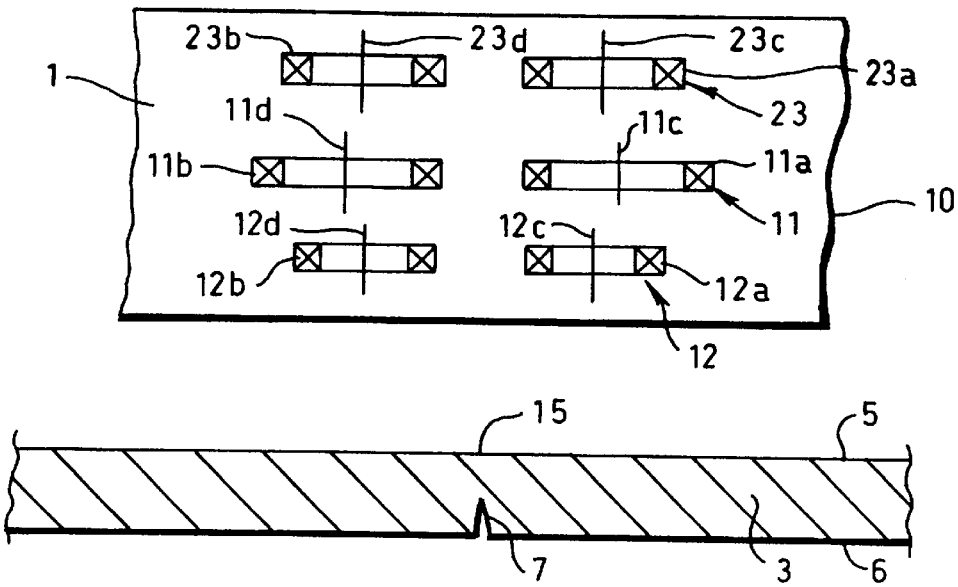
FIG. 1 shows schematically a vertical section of a probe and an object of electrically conducting material.
Figure 2:
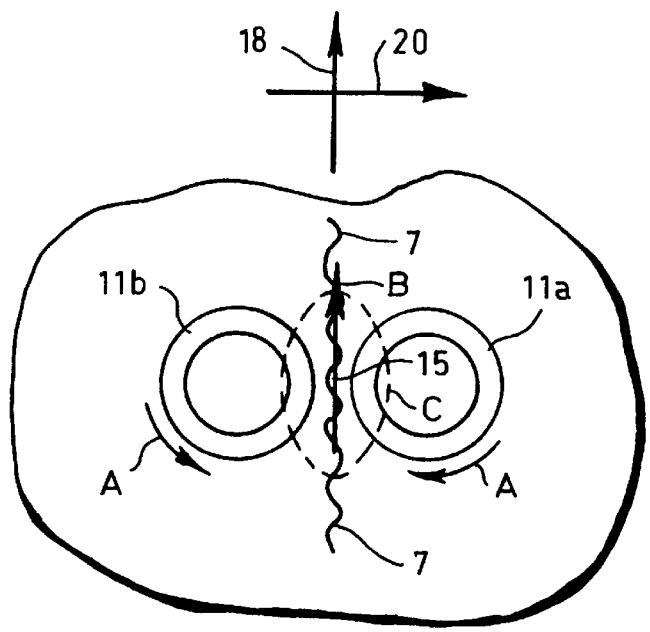
FIG. 2 shows schematically a top view of the transmitter and the near surface of the object.

Reference is made to FIGS. 1 and 2. A probe 1 is arranged near an object of electrically conducting material in the form of a flat plate 3. The object 3 of electrically conducting material has a near surface 5 (nearest to the probe 1) and a far surface 6. The plate 3 has a crack 7 that extends in a direction perpendicular to the plane of drawing at the far surface 6.

The probe 1 comprises a box 10. In the box 10 are arranged a transmitter 11 and a receiver system comprising a receiver 12. The transmitter 11 comprises two coils 11a and 11b, of which the central axes 11c and 11d are parallel to each other. The coils 11a and 11b have a diameter that is not smaller than the distance between the probe 1 and the near surface 5 of the object 3 or, more specific, the distance between the transmitter 11 and the near surface 3. The lateral spacing between the coils 11a and 11b is, at most, equal to the diameter of the coils 11a and 11b, and suitably between 10 and 90% of the diameter.

The receiver 12 comprises two coils 12a and 12b, of which the central axes 12c and 12d are parallel to each other. The diameter of the coils 12a and 12b is smaller than the diameters of the coils 11a and 11b, the diameter ratio being in the range of from 50 to 90%. The lateral spacing between the coils 12a and 12b is at most equal to the diameter of the coils 12a and 12b, and suitably between 10 and 90% of the diameter.

The transmitter 11 is connected to a device (not shown) for energizing the transmitter 11, and the receiver system is connected to a device (not shown) for recording the signals from the receiver system.

During normal operation, a set of points is selected on the near surface 5 of the object, at which points the inspection is to be carried out. In the Figure, one of the points is referred to with reference numeral 15.

Then a first direction and a second direction are selected so that the first direction is parallel to the expected longitudinal anomaly 7 and a second direction is perpendicular to the first direction. The first is referred to with reference numeral 18 and the second with reference numeral 20.

The probe 1 is positioned at the selected inspection point 15, and the transmitter is activated by allowing currents to flow through the coils 11a and 11b in a direction indicated by the arrows A. Then eddy currents are induced in the object 3 by abruptly interrupting de-energizing the transmitter 11. Energizing and abruptly de-energizing the transmitter is a way of activating the transmitter to induce transient eddy currents in the object.

As a result of the arrangement of the coils 11a and 11b, the currents flowing in the direction of the arrows A produce a resulting current in the direction of the arrow B. A further result is that the intensity of the eddy currents is located in a region C having an elliptical shape around a point in between the two coils 11a and 11b. The region C is the footprint area of the probe that is not rotational symmetric. The longer axis of the footprint C is parallel to the arrow B. For practical purposes, the size of the footprint in the object (indicated by the dashed line) is the size of the area in which the eddy currents are greater than 30% of the maximum value. The longer axis of the foot print C is also the principal direction of the eddy currents.

The probe 1 is so oriented that the footprint is directed in the first direction 18. This is the position shown in FIG. 2.

The eddy currents induced in the plate 3 generate an electromagnetic field, and the next step is determining a characteristic value of the electromagnetic field with the probe 1 in the first direction 18.

A first way in which the characteristic value of the electromagnetic field is determined comprises making a recording of the decay of the eddy currents as detected by the receiver 12 and determining the critical time. The critical time is the time it takes for the eddy currents that diffuse through the plate 3 to reach the far surface 6. The critical time in the first direction is $\tau_{crit1}$.

Having done that, the probe 1 is rotated over 90°, so that the probe is directed in the second direction 20 at the selected inspection point 15. Again the transmitter is energized by allowing currents to flow through the coils 11a and 11b in a direction indicated by the arrows A and de-energized. The principal direction of the eddy currents is now directed in the second direction 20. Then the critical time in the second direction is determined, $\tau_{crit2}$.

A combination of the characteristic values in the first and second direction is determined, which is in this case the quotient, $\alpha$, of the critical times $\tau_{crit1}$ and $\tau_{crit2}$.

For each of the inspection points $\alpha$ is determined, and then the values of $\alpha$ for each inspection point are compared to a norm, for example the average (mean or median) value of the $\alpha$'s.

At inspection point 15, the crack 7 in the first direction 18 will be detected because the value for $\alpha$ at inspection point 15 will differ significantly from the norm.

The norm is the average (median or mean) value of the combinations of the characteristic values in the first and second direction of the entire set of inspection points.

In the specification and in the claims, a significant difference is a statistically significant difference, for example more than the standard deviation.

The quotient of the critical times can further be used to determine the depth of the crack, and this is done by comparing the quotient with a reference and obtaining the depth of the crack from the comparison.

In the above described method, the critical time was determined. However, the received signal contains more information than needed to determine the critical time. Therefore in an alternative method, determining the characteristic value in the first direction 18 of the electromagnetic field comprises the steps of making a recording $V_1$ over time of the decay of the eddy currents at the inspection point 15 detected with the receiver 12 and determining $$\overline{V}_1 = (1/n) \sum_{i=1}^{n} V_1(t_0 + (i-1)\Delta).$$

Determining the characteristic value in the second direction 20 of the electromagnetic field comprises the steps of making a recording $V_2$ over time of the decay of the eddy currents at the inspection point 15 detected with the receiver 12 and determining $$\overline{V}_2 = (1/n) \sum_{i=1}^{n} V_2(t_0 + (i-1)\Delta).$$

In these equations $t_0$ is an initial time, $\Delta$ is the sample interval and n is the number of samples that are included in the summation. The combination of the characteristic values is the quotient $\overline{V}_1/\overline{V}_2$.

In the above described methods, only one receiver is used. In a suitable alternative, the probe 1 further comprises an upper receiver 23. The receiver 12 is then referred to as the lower receiver.

The upper receiver 23 comprises two coils 23a and 23b, of which the central axes 23c and 23d are parallel to each other. The diameter of the coils 23a and 23b is smaller than the diameters of the coils 11a and 11b, the diameter ratio being in the range of from 50 to 90%. The lateral spacing between the coils 23a and 23b is at most equal to the diameter of the coils 23a and 23b, and suitably between 10 and 90% of the diameter.

Two receivers allows determining the gradient of the electromagnetic field generated by the eddy currents.

In this case the characteristic value of the electromagnetic field is a characteristic value of the gradient of the electromagnetic field.

In this case determining the characteristic value in the first direction comprises the steps of making two recordings $V_{1l}$ and $V_{1u}$ over time of the decay of the eddy currents at the inspection point using the two spaced apart receivers 12 and 23 and determining $$\alpha_1 = \frac{\sum_{i=1}^{n} V_{1u}(t_0 + (i-1)\Delta)}{\sum_{i=1}^{n} V_{1l}(t_0 + (i-1)\Delta)}.$$

Determining the characteristic value in the second direction comprises the steps of making two recordings $V_{2u}$ and $V_{2l}$ over time of the decay of the eddy currents at the inspection point using the two spaced apart receivers 12 and 23 and determining $$\alpha_2 = \frac{\sum_{i=1}^{n} V_{2u}(t_0 + (i-1)\Delta)}{\sum_{i=1}^{n} V_{2l}(t_0 + (i-1)\Delta)}.$$

In these two equations, $t_0$ is an initial time, $\Delta$ is the sample interval and n is the number of samples that are included in the summation. The combination of the characteristic values is the quotient $\alpha_1/\alpha_2$.

In the embodiment of the probe 1 as shown in FIG. 1, the receivers 12 and 23 are located one above the other in a vertical direction—perpendicular to the near surface 5 of the object 3. In an alternative embodiment (not shown) the receiver antenna means are spaced apart in a horizontal direction—parallel to the near surface 5.

In an alternative embodiment of the invention, inducing transient eddy currents is replaced by introducing alternating eddy currents. The alternating eddy currents can have a single frequency, or they can have a plurality of frequencies. In the latter case the transmitter is energized by an alternating current that is the sum of a number of sinus-shaped currents of different frequencies and suitably the sinus-shaped currents have the same amplitude. The latter method is known as multi-frequency method.

In that case determining the characteristic value in the first direction 18 comprises making a recording $V_1(t)$ of the signal of the receiver 12 with time (t) and determining the amplitude $A_1(f)$ of the signal as a function of the frequency (f) of the signal, and determining the characteristic value in the second direction 20 comprises making a recording $V_2(t)$ of the signal of the receiver 12 with time (t) and determining the amplitude $A_2(f)$ of the signal as a function of the frequency (f) of the signal. The combination of the characteristic values in the first and second direction is the quotient of the amplitudes $A_1/A_2$ for a predetermined frequency ($f_0$).

This method can, as well, be used to determine the depth of the crack. However, then it is required to use a multi-frequency signal, because the penetration depth of the electromagnetic field generated by activating the transmitter decreases with increasing frequency. Then a comparison of the quotients of the amplitudes for several frequencies with reference values will provide the depth of the crack.

Alternatively, in place of the amplitude the phase can be used. Then from the signals $V_1(t)$ and $V_2(t)$ in the first and second directions the phases $\phi_1(f)$ and $\phi_2(f)$ are determined. The combination of the characteristic values in the first and second direction is the difference of the phases $\phi_1$ and $\phi_2$ for a predetermined frequency ($f_0$).

With the alternating current method, the gradient of the electromagnetic field generated by the eddy currents can also be determined. And to this end the probe 1 also contains the upper receiver 23.

Determining the characteristic value in the first direction comprises the steps of recording the signals of the receivers with time, wherein $V_{1l}(t)$ is the signal of the lower receiver 12 with time (t) and $V_{1u}(t)$ is the signal of the upper receiver 23 with time (t), determining the amplitudes $A_u(f)$ and $A_l(f)$ of the signals as a function of the frequency of the signal and determining the quotient $\alpha_1$ of the amplitudes $A_u/A_l$ for a predetermined frequency.

Determining the characteristic value in the second direction comprises the steps of recording the signals of the receivers with time, wherein $V_{2l}(t)$ is the signal of the lower receiver 12 with time (t) and $V_{2u}(t)$ is the signal of the upper receiver 23 with time (t), determining the amplitudes $A_u(f)$ and $A_l(f)$ of the signals as a function of the frequency of the signal and determining the quotient $\alpha_2$ of the amplitudes $A_u/A_l$ for a predetermined frequency.

The combination of the characteristic values in the first and second direction is the quotient of the quotients $\alpha_1/\alpha_2$.

In the above description of the method, the step of activating the transmitter to induce eddy currents in the object such that the footprint is directed in the first or second direction by activating the transmitter is carried out by rotating the probe. In other words the probe was set at a position in the first direction, a measurement was taken and then the probe was rotated to the second direction.

Rotating the footprint can as well be done electronically, and when this electronic way is used there is no need to rotate the probe itself.

Figure 3:
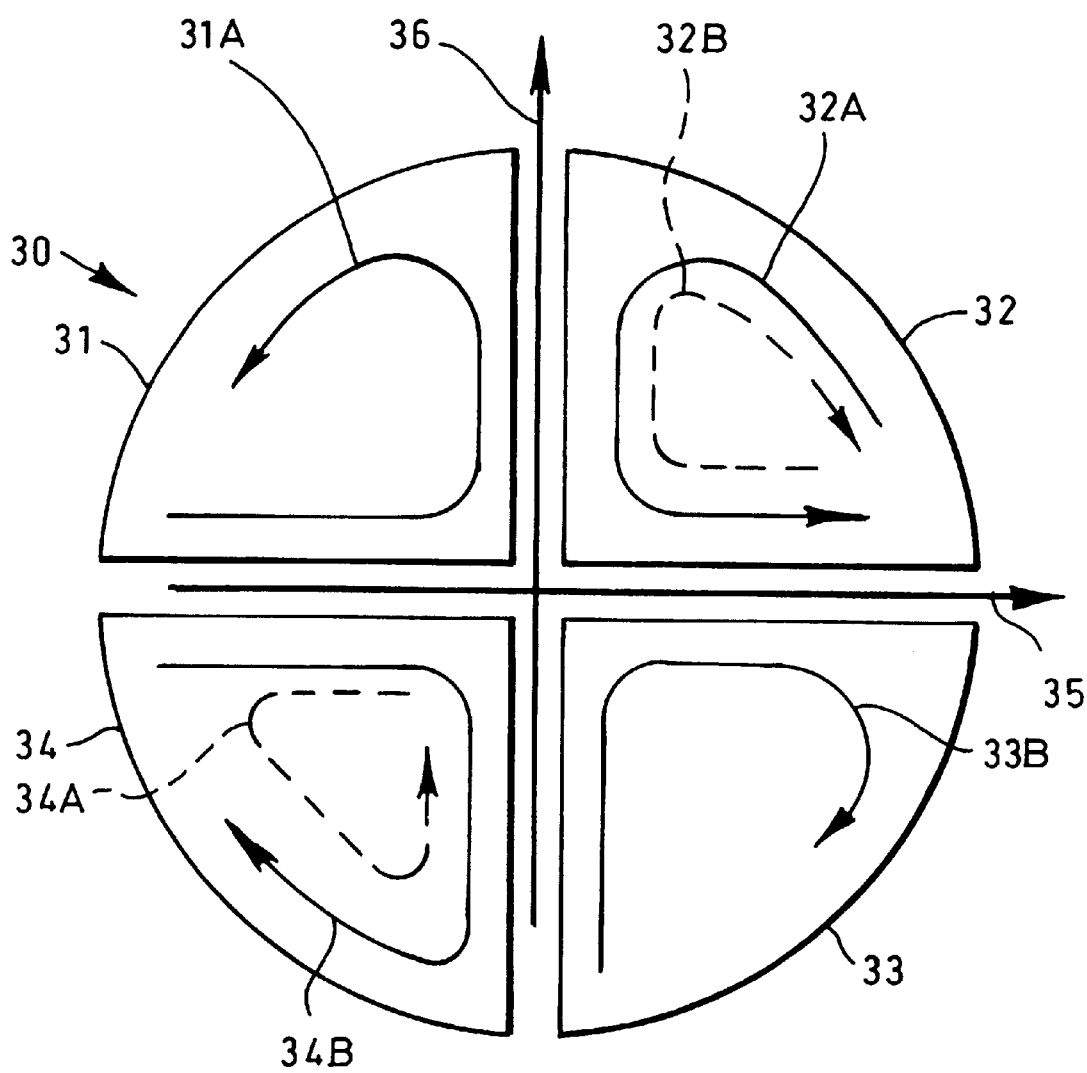
FIG. 3 shows an alternative design of the transmitter.

Reference is now made to FIG. 3, which shows a top view of a transmitter 30 consisting of four adjacent coils 31, 32, 33 and 34. Each of the adjacent coils 31—34 have the shape of a segment of a circle. Energizing the transmitter 30 is done in two ways, at first opposing coils 31 and 33 are energized by currents flowing in opposite directions 31A (counter-clockwise) and 33B (clockwise) and opposing coils 32 and 34 are energized in opposite directions 32A (counter-clockwise) and 34B (clockwise). Thus the magnetic field generated by the currents flowing through the coils is directed in a first direction 35. In this way, the transmitter is activated so as to induce eddy currents in the object such that the footprint is directed in the first direction.

In order to rotate the footprint, the sense in which opposing coils 32 and 34 are energized is changed such that the currents flow in opposite directions 32B (clockwise) and 34A (counter clockwise). Thus the 10 magnetic field generated by the currents flowing through the coils is directed in a second direction 36. In this way, the transmitter is activated so as to induce eddy currents in the object such that the footprint is directed in the second direction.

When a receiver coil is used, the signal is indicative of changes in the strength of the magnetic field. However, when the receiver is a Hall effect transducer, or when the signal from the coil is integrated, the signal is indicative of the strength of the magnetic field.

For the sake of completeness, we would observe that not all transmitters, which provide a footprint that is not rotational symmetric, provide a footprint wherein the eddy currents have a principle direction. An example of such a transmitter is a single elongated coil. When this coil is energized, eddy currents will be induced in the direction of the current flowing through the elongated coil. The footprint is not rotational symmetric, but these eddy currents do not have a principal direction.

The method of the present invention provides a simple way of detecting the presence of an anomaly, wherein only one inspection technique is used. The method is suitably applied when the object is covered by a relatively thick layer of material that is not electrically conductible. The method of the present invention can not only be used to provide information about longitudinal anomalies: it can also be used to provide information about circular anomalies, provided that the probe is located at a side of the anomaly or that the probe partially covers the anomaly.

What is claimed is:

1. A method of detecting the presence of an anomaly of an object of electrically conducting material using a probe, which probe comprises a transmitter which can be activated so as to induce eddy currents in the object in a footprint area that is not rotational symmetric, and in which footprint area the eddy currents have a predetermined principal direction, wherein the transmitter comprises a pair of adjacent transmitter coils, and wherein activating the transmitter comprises energizing the pair of transmitter coils by mutually opposite currents, and which probe further comprises a receiver system for providing a signal indicative of the strength of an electromagnetic field or of changes of the strength of an electromagnetic field, which method comprises the steps of:

a) selecting a set of points on the surface of the object nearest to the probe, which points are to be inspected;

b) selecting a first inspection point from the set, and selecting a first direction and a second direction that differs from the first direction;

c) positioning the probe at the selected inspection point, activating the transmitter to induce eddy currents in the object such that the principal direction of eddy currents in the footprint area is in the first direction, and determining a characteristic value $\Phi_1$ of the electromagnetic field generated by the eddy currents;

d) activating the transmitter to induce eddy currents in the object such that the principal direction of eddy currents in the footprint area is in the second direction, and determining a characteristic value $\Phi_2$ of the electromagnetic field generated by the eddy currents;

e) selecting a next inspection point from the set and repeating steps c) and d) until all inspection points have had their turn; and f) inferring that an anomaly is present at an inspection point if a combination of the characteristic values $\Phi_1$ and $\Phi_2$ pertaining to the first and second direction deviates significantly from a norm.

2. The method according to claim 1, wherein the anomaly is an elongated anomaly, wherein the angle between the first direction and the expected elongated anomaly differs from the angle between the second direction and the expected elongated anomaly.

3. The method according to claim 2, wherein the first direction is parallel to the direction of the expected elongated anomaly and the second direction is perpendicular to the first direction.

4. The method according to claim 3, wherein inducing eddy currents in the object includes inducing transient eddy currents in the object, wherein the receiver system comprises a single receiver, wherein determining the characteristic value comprises making a recording V(t) of the signal of the receiver with time (t) and determining the critical time from the recording V(t), and wherein the combination of the characteristic values in the first and second direction is the quotient of the critical times.

5. The method according to claim 2, wherein inducing eddy currents in the object includes inducing transient eddy currents in the object, wherein the receiver system comprises a single receiver, wherein determining the characteristic value comprises making a recording V(t) of the signal of the receiver with time (t) and determining the critical time from the recording V(t), and wherein the combination of the characteristic values in the first and second direction is the quotient of the critical times.

6. The method according to claim 5, wherein the anomaly is a crack, which method further comprises comparing the quotient of the critical times in the first and second direction with a reference and obtaining the depth of the crack from the comparison.

7. The method according to claim 1, wherein inducing eddy currents in the object includes inducing transient eddy currents in the object, wherein the receiver system comprises a single receiver, wherein determining the characteristic value comprises making a recording V(t) of the signal of the receiver with time (t) and determining the critical time from the recording V(t), and wherein the combination of the characteristic values in the first and second direction is the quotient of the critical times.

8. The method according to claim 7, wherein the anomaly is a crack, which method further comprises comparing the quotient of the critical times in the first and second direction with a reference and obtaining the depth of the crack from the comparison.

9. The method according to claim 7, wherein the receiver system comprises a receiver coil, and wherein the signal represents the change of the eddy current, and wherein V is the voltage at the terminals of the receiver coil.

10. The method according to claim 1, wherein inducing eddy currents in the object includes inducing transient eddy currents in the object, wherein the receiver system comprises a single receiver, wherein determining the characteristic value comprises making a recording V(t) of the signal of the receiver with time (t) and determining the average $$\overline{V} = (1/n) \sum_{i=1}^{n} V(t_0 + (i-1)\Delta),$$

wherein $t_0$ is an initial time, $\alpha$ is the sample interval and n is the number of samples that are included in the summation, and wherein the combination of the characteristic values is the quotient of the averages in the first and second direction.

11. The method according to claim 1, wherein inducing eddy currents in the object includes inducing alternating eddy currents in the object, wherein the receiver system comprises a single receiver, wherein determining the characteristic value comprises making a recording V(t) of the signal of the receiver with time (t) and determining the amplitude of the signal as a function of the frequency of the signal, and wherein the combination of the characteristic values in the first and second direction is the quotient of the amplitudes for a predetermined frequency.

12. The method according to claim 1, wherein the anomaly is a crack, wherein inducing eddy currents in the object includes inducing multi-frequency alternating eddy currents in the object, wherein the receiver system comprises a single receiver, wherein determining the characteristic value comprises making a recording V(t) of the signal of the receiver with time (t) and determining the amplitude of the signal as a function of the frequency of the signal, and wherein the combination of the characteristic values in the first and second direction is the quotient of the amplitudes for a predetermined frequency, which method further comprises comparing the quotient of the amplitudes for several frequencies with a reference and obtaining the depth of the crack from the comparison.

13. The method according to claim 1, wherein inducing eddy currents in the object includes inducing alternating eddy currents in the object, wherein the receiver system comprises a single receiver, wherein determining the characteristic value comprises making a recording V(t) of the signal of the receiver with time (t) and determining the phase of the signal as a function of the frequency of the signal, and wherein the combination of the characteristic values in the first and second direction is the difference of the phases for a predetermined frequency.

14. The method according to claim 1, wherein the probe contains two spaced apart receivers, and wherein the characteristic value of the electromagnetic field determined in step d) is a characteristic value of the gradient of the electromagnetic field.

15. The method according to claim 14, wherein inducing eddy currents in the object includes inducing transient eddy currents in the object, wherein determining the characteristic value comprises the steps of recording the signals of the receivers with time, wherein $V_u(t)$ is the signal of the first receiver with time (t) and $V_1(t)$ is the signal of the second receiver with time (t), and determining the characteristic value $$\alpha = \frac{\sum_{i=1}^{n} V_u(t_0 + (i-1)\Delta)}{\sum_{i=1}^{n} V_l(t_0 + (i-1)\Delta)},$$

wherein $t_0$ is an initial time, $\alpha$ is the sample interval and n is the number of samples that are included in the summation, and wherein the combination of the characteristic values is the quotient of the characteristic values $\alpha$ in the first and second direction.

16. The method according to claim 14, wherein inducing eddy currents in the object includes inducing alternating eddy currents in the object, wherein determining the characteristic value comprises the steps of recording the signals of the receivers with time, wherein $V_u(t)$ is the signal of the first receiver with time (t) and $V_1(t)$ is the signal of the second receiver with time (t), determining the amplitudes of the signals as a function of the frequency of the signals and determining the quotient $\alpha$ of the amplitudes for a predetermined frequency, and wherein the combination of the characteristic values in the first and second direction is the quotient of the quotients $\alpha$.

17. The method according to claim 14, wherein the receiver system comprises a first receiver coil and a second receiver coil that is spaced apart from the first receiver coil, and wherein the signal represents the change of the eddy current, and wherein $V_1$ and $V_2$ are the voltages at the terminals of the first and second receiver coil, respectively.

18. The method according to claim 1, wherein the norm is the average (median or mean) value of the combinations of the characteristic values in the first and second direction of the entire set of inspection points.

19. The method according to claim 1, wherein each coil of the pair of transmitter coils has a diameter that is substantially equal to the distance between the probe and the nearest surface of the object.

20. The method according to claim 1, wherein the transmitter consists of four adjacent coils, each having the shape of a segment of a circle, wherein activating the transmitter to induce eddy currents in the object such that the footprint is directed in the first direction comprises activating a pair of opposing coils in opposite directions and activating the other pair in opposite directions, and wherein activating the transmitter to induce eddy currents in the object such that the footprint is directed in the second direction comprises changing the directions in which the two coils of the other pair are energized to their opposites.

* * * * *